United States Patent [19]
Devillez

[11] Patent Number: 5,958,984
[45] Date of Patent: *Sep. 28, 1999

[54] METHOD AND COMPOSITION FOR SKIN TREATMENT

[76] Inventor: Richard L. Devillez, DCDT 2220 CR 467, Hondo, Tex. 78861

[*] Notice: This patent is subject to a terminal disclaimer.

[21] Appl. No.: 09/009,724

[22] Filed: Jan. 21, 1998

Related U.S. Application Data

[63] Continuation-in-part of application No. 08/729,279, Oct. 10, 1996, Pat. No. 5,736,582.

[51] Int. Cl.⁶ .......................... A61K 31/19; A61K 33/40
[52] U.S. Cl. ......................... 514/714; 514/859; 514/846
[58] Field of Search ..................... 514/714, 828, 514/846, 848, 859

[56] References Cited

U.S. PATENT DOCUMENTS

| | | |
|---|---|---|
| 825,883 | 7/1906 | Heinrici . |
| 959,605 | 5/1910 | Queisser . |
| 1,002,854 | 9/1911 | Liebknecht . |
| 1,058,070 | 4/1913 | Liebknecht . |
| 1,139,774 | 5/1915 | Knox . |
| 3,954,974 | 5/1976 | Herzog et al. . |
| 4,363,815 | 12/1982 | Yu et al. ................................. 424/274 |
| 4,431,631 | 2/1984 | Clipper et al. . |
| 4,438,102 | 3/1984 | Ganci . |
| 4,812,173 | 3/1989 | Tsao et al. . |
| 4,826,681 | 5/1989 | Jaquet et al. . |
| 5,336,432 | 8/1994 | Petchul et al. . |
| 5,380,764 | 1/1995 | Herzog . |
| 5,393,526 | 2/1995 | Castro . |
| 5,736,582 | 4/1998 | Devillez ................................. 514/859 |
| 5,843,998 | 12/1998 | Song et al. ............................. 514/588 |

FOREIGN PATENT DOCUMENTS

| | | |
|---|---|---|
| 502459 | 3/1939 | United Kingdom . |
| WO 91/08981 | 6/1991 | WIPO . |

*Primary Examiner*—Peter F. Kulkosky
*Attorney, Agent, or Firm*—Richard C. Litman

[57] ABSTRACT

Compositions and processes for medicating human skin disorders using hydrogen peroxide as an active antimicrobial agent. The composition includes essentially hydrogen peroxide, a non-volatile carrier-solvent, and water. A predetermined final hydrogen peroxide concentration is achieved through evaporation of water. In this manner, hydrogen peroxide concentration may be controlled to avoid deleterious effects. Other therapeutic agents such as alpha hydroxy acids may also be added to the composition for treating various skin ailments.

4 Claims, No Drawings

METHOD AND COMPOSITION FOR SKIN TREATMENT

CROSS-REFERENCE TO RELATED APPLICATION

This application is a continuation in part of U.S. patent application Ser. No. 08/729,279 filed Oct. 10, 1996, now U.S. Pat. No. 5,736,582.

BACKGROUND OF THE INVENTION

1. Field of the Invention

The present invention relates to a method and composition for controlling the delivery of nascent oxygen from a hydrogen peroxide source, and particularly relates to peroxide remedies for treating skin disorders or abnormalities.

2. Description of the Related Art

Contacting the skin with nascent oxygen is a treatment regime in common use for various skin disorders. For example, nascent oxygen in contact with the skin reduces live bacteria populations, and consequently such contact alleviates skin disorders resulting from the presence of active bacteria populations. A common method for introducing nascent oxygen to the epidermis or skin is by way of benzoyl peroxide as an oxygen source material. However, the use of benzoyl peroxide as an oxygen source has disadvantages. In particular, benzoyl peroxide is unstable in most solvents. This instability limits opportunities for formulating compositions having optimum performance characteristics.

Insofar as the previous patents relating to the use of peroxide compositions for skin treatment are concerned, U.S. Pat. No. 1,139,774 to Knox discloses a system wherein concentrated hydrogen peroxide treatment of the skin is accomplished by the use of a hydrogen peroxide dispersion in paraffin. The mixture is incorporated within a surgical dressing.

Additionally, U.S. Pat. No. 825,883 to Heinrici discloses a stable solution of hydrogen peroxide. Amide compounds were therein found to stabilize hydrogen peroxide against decomposition.

Further, U.S. Pat. No. 959,605 to Queisser discloses a skin treating composition comprising a carrier and hydrogen peroxide. The carriers are disclosed to be vegetable substances such as tragacanth, agar-agar gum, gum arabic and the like. These materials are said to lower the rate of hydrogen peroxide decomposition.

Moreover, U.S. Pat. No. 3,954,974 to Herzog et al. discloses a disinfectant for the surface of human skin comprising an oil-in-water emulsion of hydrogen peroxide in the continuous aqueous phase, and a dispersed, oil phase containing suitable hydrophobic organic substances.

U.S. Pat. No. 5,380,764, which issued to Herzog on Jan. 10, 1995, discloses a composition of vitamin A, glucose and hydrogen peroxide for cosmetic and pharmaceutical use. The composition consists essentially of Vitamin A or ester, glucose, and a stable aqueous emulsion of hydrogen peroxide. It does not disclose the use of a carrier-solvent for hydrogen peroxide, or the use of alpha hydroxy acids.

Jacquet, et al., in U.S. Pat. No. 4,826,681 issued on May 2, 1989, discloses an anhydrous solution of hydrogen peroxide in an organic solvent and the use of the same in therapeutic and cosmetic formulations. The solution contains less than 1% water, with hydrogen peroxide concentrations remaining constant during use.

Liebknecht, in U.S. Pat. No. 1,002,854, discloses a method of producing a stable solution of hydrogen peroxide by mixing therewith a compound containing a carboxyl group attached to an aromatic moiety. Examples are salicylic acid, phthalic acid and derivatives thereof. Further, in U.S. Pat. No. 1,058,070, Liebknecht teaches that benzene sulfonic acid and other similar organic acids have a stabilizing effect on hydrogen peroxide.

U.S. Pat. No. 5,393,526, which issued to Castro on Feb. 28, 1995, discloses cosmetic compositions that include alpha hydroxy acids, but does not include hydrogen peroxide.

In published International Patent Application No. W 91/08981 to Aquaclear International, aqueous stabilizing solutions are disclosed for stabilizing hydrogen peroxide comprising citric acid, tartaric acid, a chelating agent and/or a buffer. The chelate inhibits metal ions from catalyzing decomposition of hydrogen peroxide.

Clipper et al, in U.S. Pat. No. 4,431,631, disclose a mouth wash composition containing hydrogen peroxide, glycerin and/or sorbitol. A nonionic surfactant is included. Flavorants and colorants present in mouth washes are said to aid in the decomposition of hydrogen peroxide. However, some selected flavorants and colorants are said to be less active than others in contributing to the decomposition of hydrogen peroxide.

A skin treating composition is described in U.S. Pat. No. 4,438,102 to Ganci, which is comprised of hydrogen peroxide, ammonium hydroxide, thioglycolic acid and a lower molecular weight alkanol. The claims are drawn to a method of promoting skin growth in mammals. Solvents mentioned in the disclosure are ketones, ethers and amines. Nothing is mentioned regarding stabilizing hydrogen peroxide against decomposition.

A hydrogen peroxide composition designed essentially for disinfecting an organic polymer product is disclosed by U.S. Pat. No. 4,812,173 to Tsao et al. Primary and secondary stabilizers for hydrogen peroxide are disclosed. Secondary stabilizers may be those from the group of propylene glycol, polyacrylic acid, diethylene glycol and sodium polyphosphate. Such compounds are not indicated to be solvents for hydrogen peroxide.

A composition containing hydrogen peroxide used as a micro-emulsion gel for antiseptic and bleaching purposes is disclosed by Petchul et al. in U.S. Pat. No. 5,336,432. The disclosure contains nothing regarding stabilizing hydrogen peroxide and controlling release of oxygen therefrom.

None of the above inventions and patents, taken either singly or in combination, is regarded to describe, suggest or render obvious the instant invention as claimed.

SUMMARY OF THE INVENTION

Accordingly, it is a principal object of the invention to provide hydrogen peroxide compositions and methods of use, principally for treating skin infirmities or disorders such as acne, for example. By the use of the compositions and methods described herein, the concentration of hydrogen peroxide at the interface between the hydrogen peroxide treating composition and the skin is controllable, resulting in release rates of oxygen which are not sufficient to produce injurious effects from excessive nascent oxygen evolution, but which are sufficient to provide antiseptic, antibacterial and/or antiviral activity.

Briefly described, a controlled delivery protocol of nascent oxygen from hydrogen peroxide compositions is accomplished through the use of an appropriate mixture of hydrogen peroxide and a carrier therefor, which carrier is a nonvolatile solvent, nonvolatile diluent or nonvolatile dispersant for hydrogen peroxide and is miscible with water in all proportions. The term "nonvolatile" is hereinafter specifically defined.

It is another object of the invention to provide compositions and methods for the controlled application of active therapeutic ingredients for topical skin treatment.

It is a further object of the invention to provide a method of delivering active therapeutic agents, such as hydrogen peroxide, to a skin treatment site in a controlled and effective manner.

It is still another object of the invention to provide compositions for treating skin conditions wherein hydrogen peroxide concentration is controlled during the time the composition is in use.

It is thus an object of the invention to provide improved composition, based on hydrogen peroxide and other active ingredients, and methods of use thereof in methods of dermatological treatments which are inexpensive, dependable and fully effective in accomplishing the intended purposes.

These and other objects of the present invention will become readily apparent upon further review of the following specification and description.

DETAILED DESCRIPTION OF THE PREFERRED EMBODIMENTS

The present invention is directed to improved hydrogen peroxide skin treating compositions and methods.

As stated previously, a common method in use for delivering nascent oxygen or free-radical oxygen to the surface of the skin is to employ benzoyl peroxide as a source agent for peroxide, which consequently produces nascent oxygen.

Benzoyl peroxide decomposes at the skin interface to yield one mole of nascent oxygen and two moles of benzoic acid. Since benzoyl peroxide has a molecular weight of about 242, the compound thus contains about 6.6% nascent oxygen per mole.

Hydrogen peroxide, on the other hand, having a molecular weight of about 34, provides about 47% nascent oxygen per mole. Thus, about three moles of hydrogen peroxide contains the same amount of nascent oxygen as 21 moles of benzoyl peroxide. Stated another way, a 3% solution of hydrogen peroxide would contain about the same amount of nascent, or free-radical, oxygen as a 21% solution of benzoyl peroxide.

Moreover, the ratio between the amount of benzoic acid yielded by benzoyl peroxide and nascent oxygen provided upon decomposition is fixed. However, by using hydrogen peroxide as the source agent for nascent oxygen, combined with a carboxylic acid such as, for example, lactic, glycolic, salicylic or benzoic acid, and the nonvolatile carrier materials described herein, the ratio between the carboxylic acid and nascent oxygen produced is variable and controllable. This allows the formulator to design compositions possessing optimum nascent oxygen release rates for a particular clinical need in question. Thus, it would be more efficient to use hydrogen peroxide, rather than benzoyl peroxide, as a nascent oxygen source if the rate of oxygen delivery to the skin site were controllable.

As pointed out previously, benzoyl peroxide is unstable in most solvents. Therefore, the dermatological formulator is limited is his or her ability to prepare compositions capable of optimum therapeutic performance of this nascent oxygen source material.

However, it has been discovered that if aqueous solutions of hydrogen peroxide are combined with certain non-volatile materials which have solvent properties with respect to hydrogen peroxide, and/or certain other materials having penetrating and miscibility enhancing properties, and are fully miscible with water, it is possible to prepare stable pharmaceutical hydrogen peroxide compositions. In the present disclosure, the expression "non-volatile solvent" refers to a material capable of dissolving hydrogen peroxide and having a vapor pressure at 25° C. of 4 mm Hg or below. As examples of materials falling within the scope of those the inventor has found to be effective nonvolatile solvents or dispersants are alcohol compositions, dimethyl isosorbide, lower molecular weight alkyl or alkylene polyols, such as propylene glycol, dipropylene glycol, 1,4-butylene glycol and glycerol. Further, higher molecular weight alkylene glycols may also be used, such as polyethylene glycol. Additionally, ether derivatives of lower m.w. alkylene glycols may be used. For example, ethylene glycol monobutyl ether is suitable. Also included are polyethylene oxide adducts of polyols. The materials used must be miscible with water in all proportions and possess the vapor pressure property described.

In general, materials useful in formulating stable mixtures of hydrogen peroxide are those having solubilizing properties with respect to hydrogen peroxide, and further those which possess a vapor pressure at 25° C. which is equal to or below 4 mm of mercury, and are miscible with water in all proportions. Additionally, the carrier material must not itself contribute to injurious skin effects.

In general, with respect to skin treating compositions, the concentration of the soluble nonvolatile, active ingredients in such compositions, when they contain a volatile solvent such as water as a carrier for the active material, will vary in an uncontrolled manner when applied to the skin. Through experimentation, it has been determined that a variety of conditions may affect the concentration of the active ingredient as the time duration of the disposition of the treating agent upon the skin increases. For example, under conditions of occlusion, wherein the treating composition is contained within a relatively closed environment, such as within a non-porous bandage, the original concentration of active therapeutic agent may decrease as a result of transepidermal fluids becoming admixed therewith. Moreover, in the opposite fashion, under unprotected application conditions, the volatile solvent may evaporate, allowing the original concentration of active agent to increase to as much as 100%.

Further, in compositions where the carrier for the active ingredient comprises a mixture of volatile solvents, the different respective evaporation rates of such solvent-carriers may result in an alteration of the carrier composition containing the active agent, which can ultimately result in an increase in the concentration of the active ingredient. The aforesaid scenario may occur if the active ingredient is poorly soluble in the carrier component having a lower volatility. As the carrier component having a higher volatility evaporates, the concentration of the active ingredient may increase to its saturation point and remain at that level, and any excess of the active ingredient will precipitate as a highly concentrated active material.

To be sure, by altering the ratio of volatile carrier solvent mixtures, and by altering the composition thereof also, the concentrations of one or more active ingredients carried within such systems may be designed to have widely varying therapeutic properties. Nevertheless, the presence in and on the skin of salts, acidic or basic materials and the occurrence of other conditions will affect the concentration profile of the active ingredient in contact with the skin. It is pointed out that the concentration of an active, therapeutic ingredient, particularly an active ingredient which is highly effective at lower concentrations, but which is deleterious to the skin at higher concentrations, may have profound effects upon pharmacological activity, absorption properties and skin irritation potential.

It has been discovered that if a carrier material for hydrogen peroxide skin treating compositions is selected from a group of materials which have solvent properties for hydrogen peroxide, have a sufficiently low volatility and are miscible with water in all proportions, the concentration of hydrogen peroxide at the skin surface may be controlled, allowing the formulator to produce skin treating compositions wherein the maximum safe concentration of hydrogen peroxide may be established for almost any required clinical treatment.

Formulating hydrogen peroxide compositions in the manner described herein allows the reactivity of hydrogen peroxide at the delivery site to be reliably determined, and the advantages to having such control of nascent oxygen delivery are the elimination of the deleterious effects of higher concentrations of hydrogen peroxide. Thus, once all of the compounds present at the skin surface which are capable of reacting with hydrogen peroxide at a given level of concentration have reacted therewith, the residual, remaining hydrogen peroxide in the treating composition is stable at the skin interface for an extended time duration. However, without the use of the carrier materials specified herein with hydrogen peroxide, either the compound is available for continuous reaction until it is fully consumed, or the concentration increases to injurious levels.

The concentration of hydrogen peroxide in skin treating compositions can be controlled if a carrier is selected for hydrogen peroxide which is (1) non-volatile, is (2) a solvent for hydrogen peroxide and is (3) fully miscible with water. For example, through experimental observations it has been determined that if a 6% solution of hydrogen peroxide in water were applied to the skin on a bandage, after several hours of such contact the skin tissue becomes damaged and cellular degradation occurs as the water evaporates and hydrogen peroxide becomes concentrated. However, if a 6% solution of hydrogen peroxide in water were mixed with a carrier such as dimethyl isosorbide, hydrogen peroxide concentration does not increase beyond a predictable upper level.

For example, in a skin treating composition comprising 20% of a 30% aqueous solution of hydrogen peroxide, 20% by wt. of dimethyl isosorbide and 60% water, there is 74% volatile solvent present in the form of water. Fourteen percent of the water comes from the initial hydrogen peroxide solution used, and 60% comes from additional added water. When this solvent evaporates the remaining composition is comprised of about 6 parts of hydrogen peroxide in 26 parts of total treating composition, resulting in a stable composition having about 23% hydrogen peroxide available for activity.

This scenario allows for the manufacture of skin treating compositions possessing a relatively high concentration of hydrogen peroxide at the treatment site, and the peroxide is maintained in solution. As a result of achieving relative stability in solution, it is thus prevented from injuring dermal tissue.

The aforesaid concept of combining a bio-active ingredient and nonvolatile carrier-solvent is applicable to skin bio-affecting agents or therapeutics other than hydrogen peroxide which, when present at the skin surface in greater concentrations may have deleterious or unwanted effects, but which when present in lesser concentrations have beneficial or desired effects. Some active skin treating agents falling within the above category are phenols, alkanolamines such as triethanolamine, and monoethanolamine, inorganic alkaline agents, acidic materials, urea, salicylic acid and alpha hydroxy acids.

The following examples illustrate how non-volatile carrier materials which are solvents for hydrogen peroxide may be combined with hydrogen peroxide to produce compositions containing controlled amounts of the peroxide component upon evaporation of the aqueous solvent.

Reference is made to the following Examples and Table. The initial concentration in the first column below refers to an aqueous/hydrogen peroxide composition. A standard 35% by weight hydrogen peroxide solution was diluted with water to arrive at aqueous hydrogen peroxide solutions containing, after dilution, various amounts of hydrogen peroxide, from 1 to 6 wt. percent. As shown in the table below, various aqueous compositions can be made, varying from initial hydrogen peroxide concentrations of from 1 to 6% by weight, and non-volatile carrier concentrations from 10 to 30% by weight. Once the water portion of the composition evaporates, all that is left is hydrogen peroxide in non-volatile solvent. Through manipulation of initial concentrations, the final concentration of hydrogen peroxide in non-volatile solvent can be controlled, as shown in the table. For example, the first sample was initially a 3% hydrogen peroxide, 10% non-volatile carrier aqueous solution. Upon evaporation of water, the solution becomes a maximum 3/13 or 23% solution of hydrogen peroxide in non-volatile solvent. Although the examples below used propylene glycol as the non-volatile solvent, results are equally valid for other carrier-solvent materials having the properties defined herein.

| | EXAMPLES | | |
|---|---|---|---|
| SAMPLE | INITIAL HP CONCENTRATION | NONVOLATILE CARRIER % | FINAL HP CONCENTRATION |
| 1. | 3 | 10 | 23.0 |
| 2. | 3 | 30 | 9.0 |
| 3. | 6 | 30 | 16.7 |
| 4. | 1 | 20 | 4.8 |

The following are examples of specific skin medication compositions that have been prepared and have been shown to be particularly efficacious:

| ACNE SKIN TREATMENT COMPOSITION | | DRY SKIN TREATMENT COMPOSITION | |
|---|---|---|---|
| INGREDIENTS | WT. PERCENT | INGREDIENTS | WT. PERCENT |
| Hydrogen peroxide (35%) | 10 | Hydrogen peroxide (35%) | 10 |
| Salicylic acid | 1.0 | Lactic acid | 2.0 |
| Propylene glycol | 10 | Propylene glycol | 10 |
| Cetyl alcohol | 1.6 | Cetyl alcohol | 2.0 |
| Distilled water | 74 | Distilled water | Q.S. |
| Sodium hydroxide (q.s. pH 4.6) | 0.3 | Vitamin E Acetate | 0.5 |
| Promulgen G | 1.8 | Promulgen G | 2.0 |
| Simethicone | 0.06 | Simethicone | 0.1 |

-continued

| ACNE SKIN TREATMENT COMPOSITION | | DRY SKIN TREATMENT COMPOSITION | |
|---|---|---|---|
| INGREDIENTS | WT. PERCENT | INGREDIENTS | WT. PERCENT |
| Sodium lauryl sulfate | 0.3 | Sodium lauryl sulfate | 0.3 |
| | | Sodium hydroxide | Q.S. pH 4.5 |

The above compositions may be prepared by mixing water soluble materials into the appropriate amount of water as a preliminary step, and then mixing other materials until a creamy consistency is achieved. However, one having ordinary skill in the chemical or pharmaceutical arts is capable of arriving at the most efficient manner of making the compositions herein disclosed. Further, other alpha hydroxy carboxylic acids, such as glycolic acid, or malic acid, may be substituted for salicylic acid and lactic acid in the two compositions.

Additionally, alkylene glycols, such as diethlylene glycol, 1,4-butylene glycol, and polyethylene glycol, also may be used, in concentrations of 8 to 20 percent by weight, as effective non-volatile carriers of hydrogen peroxide. These glycols are effective carriers of hydrogen peroxide at 3 to 23 percent. Alpha hydroxy acids, such as salicylic acid and lactic acid in concentrations from 0.5 to 2 percent by weight have also been used. All samples have been stable over time and have not irritated the skin in tested subjects.

The examples given above are preferred compositions. One having ordinary skill in the art is assumed to realize that the relative proportions may be altered from those shown in the above examples in order to arrive at compositions having substantially equivalent functional results.

Simethicone is an official name in the United States Pharmacopeia for dimethylpolysiloxane materials made by various suppliers. Promulgen G is a trade name for a gelling agent comprising stearyl alcohol and Ceteareth-20, made by Amerchol Corp. Germaben II is a trade name for a broad spectrum antimicrobial composition including propylene glycol, diazolidinyl urea, methyl paraben and propyl paraben made by Sutton Labs.

A clinical study was performed to ascertain the effectiveness of compositions falling within the scope of the invention as compared to those not within the scope of the invention. The results are as follows:

Name of Clinical Study: Acne Study-Hydrogen Peroxide

Ten subjects were enrolled in a study to evaluate the efficacy of a skin medication composition in which hydrogen peroxide is present in the composition in solution in a carrier-solvent for the treatment of Acne Vulgaris. The carrier has a vapor pressure of equal to or below 4 mm of Hg at 25°, and is thus substantially nonvolatile. The composition of the Acne treating composition was made in accordance with the present invention, and includes 10% hydrogen peroxide, 1% salicylic acid, and 10% propylene glycol by weight.

The trial subjects applied the above composition to acne papules and pustules twice each day for eight weeks. The subjects were not allowed to use any other topical medication or oral medication during the length of the trial period. The trial subjects were evaluated for the number of acne papules and pustules at three evaluation time periods, a baseline period, at four weeks and at eight weeks. A count of acne papules and pustules was made at each evaluation time period and the mean was reported. Comedones were not counted.

| RESULTS: MEAN COUNTS FOR ALL SUBJECTS | | |
|---|---|---|
| BASELINE | WEEK 4 | WEEK 8 |
| 18.2 | 8.5 | 4 |
| % improvement | 53% | 78% |

Adverse Events

No adverse events. The subjects reported and evinced no indication nor manifestation of burning, stinging or redness during the course of the trial period.

General Observations

It is the opinion of the administrator of this study, who is also the inventor of the present invention, that the above product, is a viable and useful product, and that it appears to be as effective as compositions containing benzoyl peroxide as an oxygen provider. Such benzoyl peroxide compositions, with the exception of a product known as Brevoxyl, are known to produce skin coloration and scaling. The present composition does not possess such effects.

Name of Clinical Study: Dry Skin Study-Hydrogen Peroxide

Five subjects were enrolled in a study to evaluate the efficacy of a skin medication composition in which hydrogen peroxide is present in the composition in solution in a carrier-solvent for the treatment of dry skin. The carrier has a vapor pressure of equal to or below 4 mm of Hg at 25°, and is thus substantially nonvolatile. Increasing the oxygen tension on the skin should result in improved healing of dry, scaly, and irritated skin. The composition of the dry skin treating composition was made in accordance with the present invention, and includes 10% hydrogen peroxide, 3% Lactic acid, and 10% propylene glycol by weight.

The trial subjects applied the above composition to dry skin twice a day, once after a morning shower and once in the evening before bed. No other topical lubricants were used by the test subjects. Subjects were allowed to use the product if itching occurred during the day. The study lasted two weeks with marked reduction in scaling and itchiness. After the first week of use, itching was reduced by greater than 50% and dryness reduced more tan 70%. After the second week, the subjects found that itching had been reduced more than 85% and dryness reduced by 95%.

Adverse Events

No adverse events. The subjects reported and evinced no indication nor manifestation of burning, stinging or redness during the course of the trial period.

General Observations

It is the opinion of the administrator of this study, who is also the inventor of the present invention, that the above product, is a viable and useful product, and that it appears to be as effective as other compositions previously used. The was evidence of quick healing of scratch wounds without any indication of infection by the end of the study.

Compositions identified using trade names in the examples herein have formulations as follows:

SIMETHICONE—A mixture of dimethicone having dimethyl siloxane units averaging 200 to 350 and hydrated silica.

PROMULGEN G—Stearyl alcohol and polyethylene glycol 1000 cetyl/stearyl ether.

It is to be understood that the present invention is not limited to the embodiments described above, but encompasses any and all embodiments defined within the scope of the following claims.

I claim:

1. A composition for treating skin disorders, whereby a predetermined maximum terminal concentration of hydrogen peroxide in a non-volatile carrier-solvent may be achieved through evaporation of water, said composition consisting essentially of:

3 to 23% by weight of hydrogen peroxide;

8 to 20% by weight of a non-volatile carrier-solvent selected from the group of alkylene glycols consisting of diethylene glycol, 1,4-butylene glycol, propylene glycol, and polyethylene glycol;

0.5 to 2% by weight of a hydroxy acid selected from the group consisting of salicylic acid, lactic acid, glycolic acid, and malic acid; and the balance water.

2. The composition for treating skin disorders as defined in claim 1 wherein said compound consists essentially of:

about 10% by weight of hydrogen peroxide;

about 10% by weight of propylene glycol, as a non-volatile carrier-solvent;

about 1.0% by weight of the alpha hydroxy acid, salicylic acid; and the balance water.

3. The composition for treating skin disorders as defined in claim 1 wherein said compound consists essentially of:

about 10% by weight of hydrogen peroxide;

about 10% by weight of propylene glycol, as a non-volatile carrier-solvent;

about 2.0% by weight of the alpha hydroxy acid, lactic acid; and the balance water.

4. A method for the treatment of skin disorders comprising the step of applying to the skin an effective amount of the composition set forth in claim 1.

* * * * *